United States Patent [19]

Olsson et al.

[11] 4,228,677

[45] Oct. 21, 1980

[54] METHOD AND MEANS FOR MEASURING SURFACE TENSION

[76] Inventors: Kjell I. Olsson, Eskilstorpsgatan 7, 235 00 Vellinge; Anders E. B. Aberg, Nyckelkroken 3, 222 47 Lund; Lars O. S. Gislen, Dala, 240 50 Ostraby, all of Sweden

[21] Appl. No.: 22,903

[22] Filed: Mar. 22, 1979

[30] Foreign Application Priority Data

Mar. 23, 1978 [SE] Sweden ............................... 7803385

[51] Int. Cl.³ .......................................... G01N 13/02
[52] U.S. Cl. ................................................. 73/64.4
[58] Field of Search ...................................... 73/64.4

[56] References Cited

U.S. PATENT DOCUMENTS

| 2,473,553 | 6/1949 | Stokes | 73/64.4 |
| 3,483,737 | 12/1969 | Jennings, Jr. et al. | 73/64.4 |

Primary Examiner—Gerald Goldberg
Assistant Examiner—Joseph W. Roskos
Attorney, Agent, or Firm—Schwartz, Jeffery, Schwaab, Mack, Blumenthal & Koch

[57] ABSTRACT

A method and means of measuring the surface tension of a liquid wherein the liquid is discharged from a liquid container by a pump. After passage through a discharge pipe, the discharged liquid enters a nozzle in which stable drops of liquid are formed. In order to determine surface tension, the pump displacement necessary to provide the amount of liquid for forming each drop is measured.

9 Claims, 4 Drawing Figures

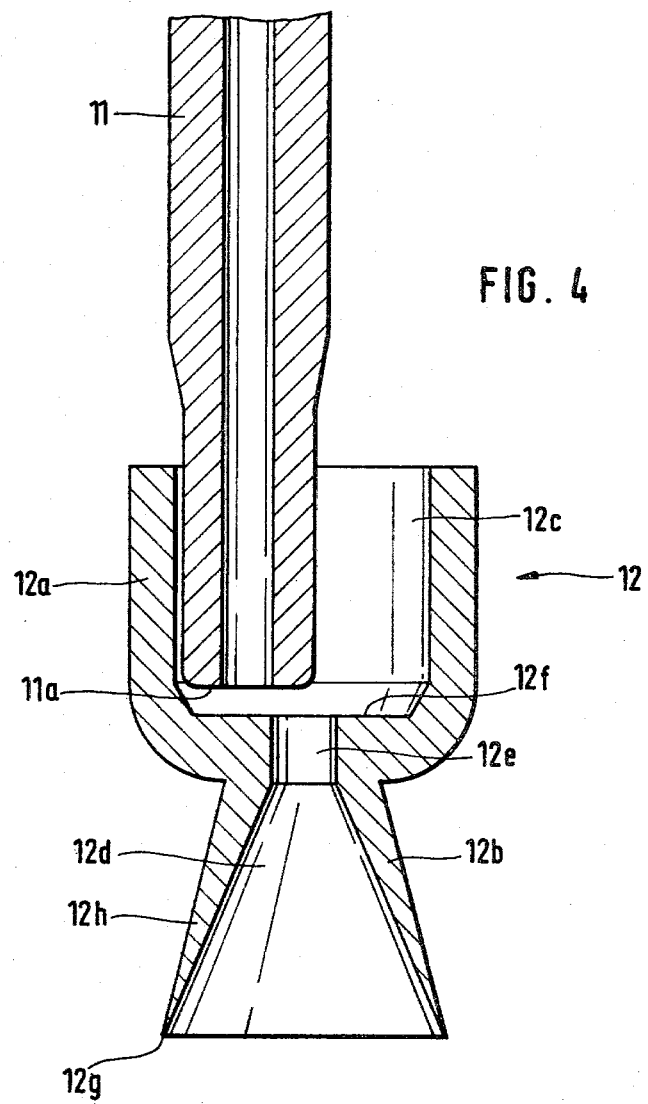

METHOD AND MEANS FOR MEASURING SURFACE TENSION

The present invention, in the first place, relates to a method of measuring the surface tension of liquids, particularly that of faetal water, in order to establish lung-ripeness or not of the faetus. In the second place, the invention relates to an instrument for carrying out the method in question.

Up till now, for measuring the lung-ripeness of faetuses, time-consuming, unwieldy and undependable methods have been utilized which has caused difficulties in clinical practice.

The present invention has for its object to provide a quick method which enables accurate measuring results to be obtained by simple means. This object, according to the invention, is obtained substantially by pressing out a predetermined number of drops of the liquid from a liquid container, and measuring the distance which the liquid in the liquid container has moved at the moment when said predetermined number of drops have left the liquid container. An instrument which is particularly well adapted for carrying out this method is obtained by the fact that a discharge nozzle through which the liquid drips from the container has a conically divergent end portion with wall portions which taper towards the extreme end to define a sharp end edge, and the nozzle having, additionally, at least one air inlet which enables air and liquid to meet before the liquid will have reached the conically divergent end portion.

The invention will now be disclosed more in detail with reference to the accompanying drawings, in which:

FIG. 1 diagrammatically illustrates an instrument according to the invention;

FIG. 4 shows a discharge nozzle forming part of the instrument.

Figure 1:
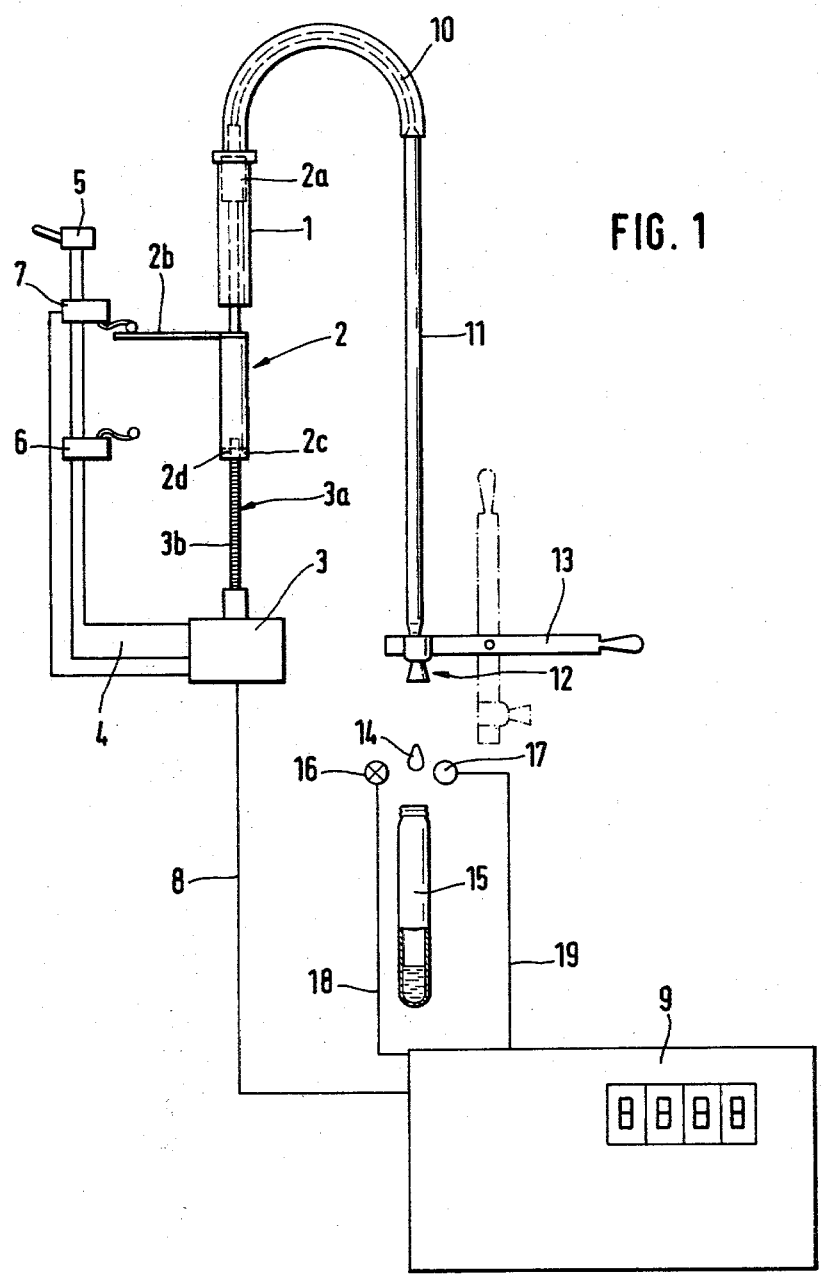

The instrument shown in FIG. 1 comprises a liquid container 1 containing a liquid, the surface tension of which is to be measured. Projecting into the liquid container 1 is the plunger 2a of a pump 2 which is operated by a step-by-step motor 3 which is connected to a source of electric current (not shown) through a circuit 4. Circuit 4 comprises a switch 5 for controlling the direction of movement of the motor 3, and thus of the pump 2. The circuit 4 further comprises two micro-type limit switches 6 and 7 adapted to be actuated by a lever 2b forming part of the pump 2. The micro-type limit switches 6 and 7 determine the length of throw of the pump 2, firstly in that the switch 6 will open circuit 4 when, on a downward throw of the pump 2, the lever 2b will reach this switch 6 and secondly in that the switch 7 will open circuit 4 when, on an upward throw of the pump 2, the lever 2b will reach the switch 7.

The motor 3 is connected through a lead 8 to a calculator 9 adapted to calculate the average pump-plunger displacement for a number of drops, for instance 10 drops.

The pump plunger 2a is adapted to force out liquid, the surface tension of which is to be measured, from the liquid container 1 into a conduit 10 connected thereto, and down into a succeeding collector pipe 11. The collector pipe 11 is adapted to discharge the liquid into a nozzle 12 which may suitably be carried by a pivoting lever 13, so that the nozzle 12 can be set into various positions relative to the collector pipe 11, for instance.

The nozzle 12 is so designed as to discharge the liquid drop-wise, and drops 14 fall from the nozzle 12 down into a collector vessel 15 while passing by a photocell device which, in a manner well-known per se, comprises light-emitting unit 16 and a pick-up unit 17, the drops 14 passing between these units. The units 16, 17 of the photocell device are connected to the calculator 9 through leads 18, 19.

In the embodiment shown, the motor 3 is provided with an axis 3a for displacing the plunger 2a of the pump 2. This axis has a thread 3b which is engaged by a corresponding thread (not shown) in a nut member 2c of the pump 2. The nut member 2c is provided with a flange 2e which is received in a recess 20 in a fixed member 21 of the instrument, whereby the nut member can not be rotated but is displaced at rotation of the axis. The lever 2b and the pump plunger 2a are mounted on the outer end of said nut member 2c.

The motor 3 rotates the axis 3a such that the nut member 2c and thereby the plunger 2a are displaced to force liquid out of the liquid container 1. When the lever 2b has reached the limit switch 7 and broken the operation of the motor 3, the collector pipe 11 may be filled with a new liquid, the surface tension of which is to be measured. For filling, the motor 3 is once again started, but so that the axis 3a rotates in the opposite direction. The filling process is completed as soon as the lever 2b reaches the limit switch 6, whereby the operation of the motor is broken.

This filling process is efficient but relatively time consuming, especially since it is often preferable to give the thread 3b of the axis 3a a smaller pitch in order to attain a very high accuracy of measurement.

Figure 2:
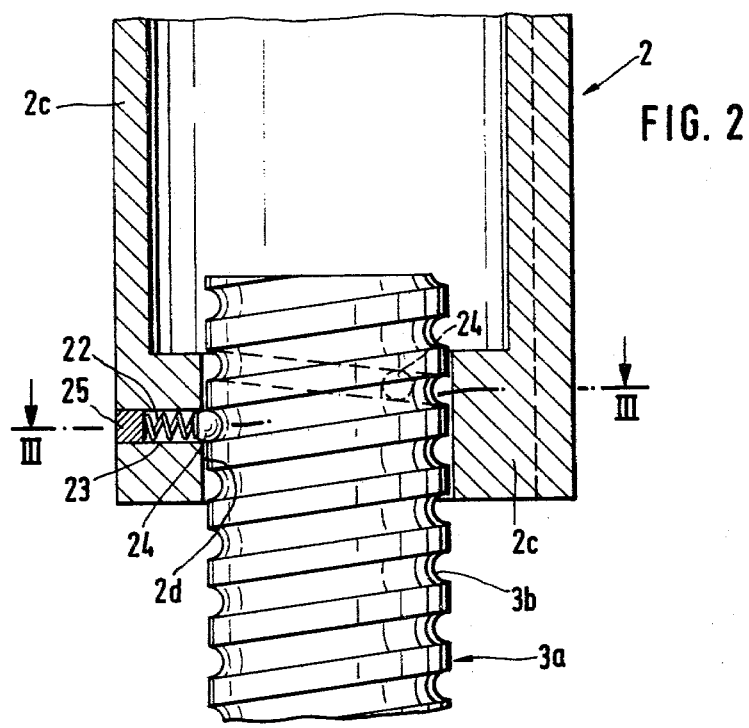
FIG. 2 shows a part of the instrument.
Figure 3:
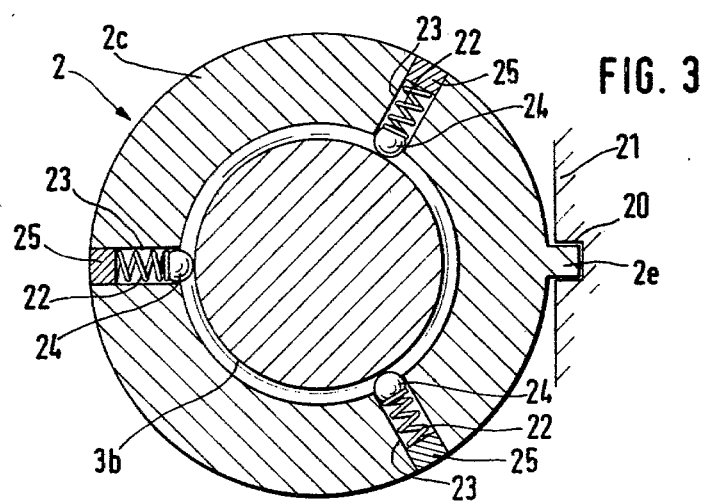
FIG. 3 is a cross-section along the line III—III in FIG. 2.

The filling process may be accelerated by means of a device illustrated in FIGS. 2 and 3. In this device, the nut member 2c has no thread for the axis 3a, but a bore 2d through which the axis extends. Furthermore, at least one spring element 22 is mounted in a bore 23 in the nut member 2c and engages on the one hand a fixed plug 25 and on the other hand a body 24, preferably a ball, and press this towards the axis 3a. The body 24 is shaped so that it may engage the thread 3b of the axis and the spring force is chosen so that the ball 24 is maintained in engagement with the thread for obtaining connection between the motor 3 and the pump plunger 2a for plunger operation and so that the plunger 2a may be pressed back to its starting position by hand. Thereby, the collector pipe may be filled very quickly, namely by pressing down the plunger 2a e.g. by means of the lever 2b. The ball 24 will then be pressed out of engagement with the thread 3b but rests finally once again in said thread for transferring the movement of the axis 3a to the pump plunger.

One spring element 22 is sufficient per se, but more than one, preferably three symmetrically arranged spring elements are provided and spaced apart so that the balls 24 thereof simultaneously engage the thread 3b of the axis.

By means of this device, time can be saved and a more simple motor 3 having only one direction of rotation may be used. Additionally, the several symmetrically arranged spring elements 22 facilitate the pressing process and prevent the thread 3b of the axis 3a from being damaged.

The nozzle 12 of FIG. 4 comprises a receiver portion 12a and a conical discharge-end portion 12b. The hollow interior 12c of the receiver portion 12a is disposed concentrically with the hollow interior 12d of the discharge-end portion 12b, these interior spaces 12c, 12d being interconnected by a centrally disposed restriction 12e.

The collector pipe 11 projects downward into the interior space 12c of the receiver portion 12a, on one hand so that the end edge 11a of the pipe 11 is disposed in spaced relation above the bottom 12f of the space 12c, and on the other hand so that the same is decentered relative to the restriction 12e. As a consequence of this construction, the liquid running down from the collector pipe 11 will contact the air before the liquid will reach the conical discharge-end portion 12b, whereby an advantageous ejector action will be obtained due to the fact that a free liquid surface will form within the receiver portion 12a.

The conically divergent discharge-end portion 12b comprises wall portions 12h which taper towards the extreme-end 12g so as to form a sharp-edged extreme end 12g. Owing to this design the drops 14 are prevented from wetting the outer surface 12b of the nozzle, thus resulting in a stable drop-formation.

Accurate values of the surface tension of the liquid are obtained by pressing out a definite number of drops 14 of the liquid from the liquid container 1, and measuring the way-length described by the liquid within the container 1 as the predetermined number of drops 14 have been discharged from the liquid container 1. The number of drops 14 is counted by the aid of the photocell-device, the units 16, 17 of which count the indicated number through leads 18, 19 to the calculator 9. Particularly correct measuring values will be obtained in a simple way by measuring the movement of the liquid in the liquid container 1 by measuring the number of pulses in the circuit 4 through which the motor 3 for operating the pump 2 is driven.

Generally, from a cleaning point of view it is unfavorable if the liquid, the surface tension of which is to be measured, should come into contact with the parts of the pump 2. This problem can be solved simply be causing the liquid in the liquid container 1 to be displaced by the pump 2 through an air cushion.

The method and instrument thus described and illustrated may be varied within the scope of the appended claims. The method, as well as the instrument, can be used for measuring the surface tension of various types of liquids and, suitably, can be used, for instance, for measuring the surface tension of faetal water to ascertain lung-ripeness of a faetus.

We claim:

1. A method of measuring the surface tension of a liquid comprising the steps of:
   (a) discharging the liquid from a liquid container by a pump;
   (b) forming a drop from the discharged liquid; and
   (c) measuring the pump displacement necessary to provide the amount of liquid required for forming the drop.

2. The method claimed in claim 1, wherein the displacement required to press out each drop of the liquid from the liquid container is measured by recording the number of pulses required to operate the pump to execute said displacement.

3. The method claimed in claim 2, characterized in that the liquid in the liquid container is displaced by the pump through the medium of an air cushion which prevents any contact between the pump and the liquid.

4. The method as claimed in claims 1, 2 or 3 a plunger of the pump is movably mounted in relation to a motor-operated driving axis for driving said plunger to force liquid out of said liquid container.

5. The method as claimed in claim 4 wherein the movement of the plunger relative the driving axis is performed by overcoming a spring force which is applied to obtain connection between said driving axis and said plunger.

6. The method as claimed in claim 1 wherein the liquid to be measured is available only in small quantities and the liquid is faetal water the surface tension of which is to be measured to ascertain lung-ripeness of a faetus.

7. A method of measuring the surface tension of a liquid comprising the steps of:
   (a) discharging the liquid from a container by a pump having a displaceable member;
   (b) operating the pump to effect said discharging step by pulses;
   (c) forming a predetermined number of drops from the discharged liquid;
   (d) recording the number of pulses required to operate the pump to execute the pump displacement needed to form the predetermined number of drops;
   (e) counting the number of drops formed with a sensing device;
   (f) calculating, in a calculating device for processing information derived from said recording and counting steps, the pump displacement to discharge each drop of liquid; and
   (g) computing, from the calculation of pump displacement to discharge each drop, the surface tension of the discharged liquid.

8. The method claimed in claim 7 wherein said step of forming a predetermined number of drops includes the further steps of:
   (a) sending the discharged liquid through and out of a liquid discharge pipe to expose the liquid to air;
   (b) directing the liquid from the discharge pipe into eccentric communication with a nozzle to enhance the exposure to air and to create an ejection action in the nozzle, which nozzle has a conically divergent discharge end; and
   (c) passing the liquid through the nozzle to form stable drops by preventing outside wetting of the device which forms the drops.

9. A device for measuring the surface tension of a liquid comprising:
   (a) a liquid container;
   (b) a pump for discharging liquid from said container, said pump having a displaceable member;
   (c) a liquid discharge pipe coupled with said pump for receiving and transporting the discharged liquid;
   (d) a nozzle disposed downstream of said dishcarge pipe in spaced, non-sealing relationship therewith for forming the discharged liquid into drops, said nozzle including a receiving portion, a flow restriction and a conically divergent end portion which tapers towards an extreme end-edge to form a sharp end-edge; and
   (e) means for measuring the pump displacement necessary to provide the amount of liquid to form a drop of discharged liquid;
   (f) whereby air may contact the liquid as it passes from the discharge pipe to the nozzle to create an ejector action and whereby the passage of liquid through the nozzle forms stable drops to be counted.

* * * * *